United States Patent [19]

Takezawa et al.

[11]  4,397,840
[45]  Aug. 9, 1983

[54] NOVEL ERYTHROPOIETIN PRODUCT AND METHOD FOR THE PREPARATION THEREOF

[75] Inventors: Kenji Takezawa, Yokohama; Hajima Hiratani, Osaka, both of Japan

[73] Assignees: Ajinomoto Co., Inc., Tokyo; Japan Chemical Research Co., Ltd., Kobe, both of Japan

[21] Appl. No.: 354,302

[22] Filed: Mar. 3, 1982

[30] Foreign Application Priority Data

Mar. 11, 1981 [JP] Japan .................................. 56-34727

[51] Int. Cl.³ ............................................. A61K 35/22
[52] U.S. Cl. ...................................... 424/99; 424/177
[58] Field of Search ................................. 424/99, 177

[56] References Cited

U.S. PATENT DOCUMENTS 4,303,650 12/1981 Takezawa et al. .................... 424/99

OTHER PUBLICATIONS

Miyake et al.-J. Biol. Chem., vol. 252, No. 15, (Aug.10, 1977), pp. 5558-5564.

Primary Examiner—Sam Rosen
Attorney, Agent, or Firm—Brisebois & Kruger

[57] ABSTRACT

The invention provides a novel erythropoietin product prepared from the urine of healthy human but exhibiting no inhibitory effect against erythropoiesis as is the most disadvantageous problem in the product prepared from the urine of healthy human. The method for the preparation of such a product comprises adsorbing the crude erythropoietin product obtained from the urine of healthy human on to a weakly basic anion exchanger from a neutral or weakly acidic aqueous solution containing 0.1 to 0.2 mole per liter of an inorganic neutral salt such as sodium chloride and then eluting the thus adsorbed ingredients with an aqueous eluant solution containing from 0.5 to 0.7 mole per liter of an inorganic neutral salt.

7 Claims, 1 Drawing Figure

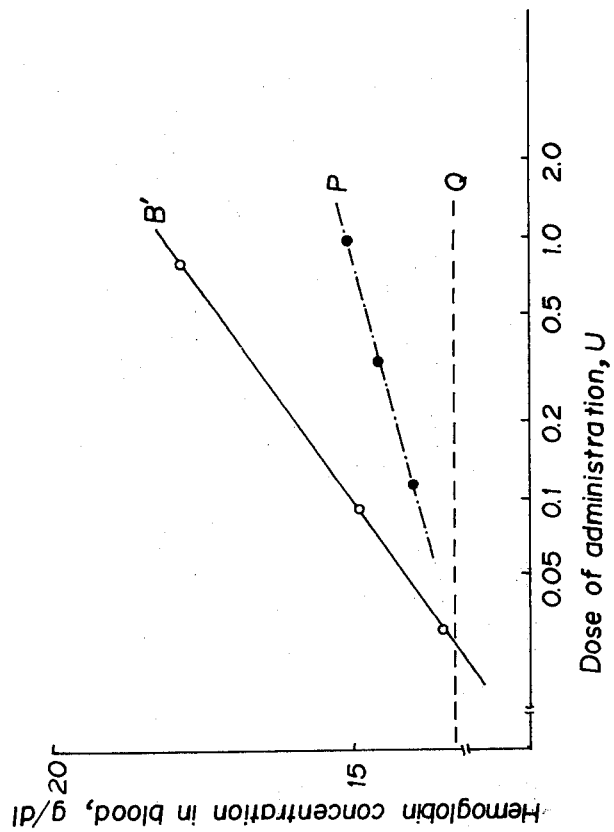

NOVEL ERYTHROPOIETIN PRODUCT AND METHOD FOR THE PREPARATION THEREOF

BACKGROUND OF THE INVENTION

The present invention relates to a novel erythropoietin product originating in the urine of healthy human and a method for the preparation thereof. More particularly, the invention relates to a novel method for the purification of the crude erythropoietin obtained from the urine of healthy human by a specific procedure to give a novel erythropoietin product exhibiting no inhibiting activity against erythropoiesis and the erythropoietin product thus prepared.

Erythropoietin is, as is well known, a hormone having an activity to stimulate erythropoiesis in a specific manner which is an indispensable factor for the differentiation of the blood stem cells into red blood corpuscles so that deficiency or decreased concentration thereof in blood causes anemia.

Therefore, erythropoietin is a promising therapeutic medicine in the clinic treatment of anemia or, in particular, renal anemia. Unfortunately, the use of erythropoietin is not so prevailing in the practical therapy due to the low availability thereof.

The hitherto undertaken method for the preparation of erythropoietin products is almost exclusively the concentration and purification of the urine of the patients of high erythropoietin secretion suffering from aplastic anemia and the like diseases. Because of the limited supply of such patient urine as an obstacle to the practical use of erythropoietin, it is highly desirable to prepare erythropoietin products from the urine of healthy human available in large volumes. A problem in the use of the urine of healthy human is the low content of erythropoietin therein in comparison with the patient urine. In addition, the urine of healthy human contains certain inhibiting factor against erythropoiesis in a considerably high concentration so that no satisfactory therapeutic effect would be obtained even if the erythropoietin product prepared from the urine of healthy human be administered to a patient of anemia.

The inventors have previously proposed a successful method for the preparation of an erythropoietin product from the urine of healthy human (see U.S. Pat. No. 4,303,650) but the erythropoietin product prepared by the proposed method still has the above mentioned problem of the inhibition against erythropoiesis and was not sufficient to satisfy the therapeutic requirement for anemia.

SUMMARY OF THE INVENTION

It is therefore an object of the present invention to provide a novel erythropoietin product having high erythropoietic activity but exhibiting no inhibitive effect to erythropoiesis, which originates in the urine of healthy human and is quite different from the conventional erythropoietin products prepared from the patient urine.

Another object of the invention is to provide a novel method for the preparation of the above mentioned erythropoietin product useful as a therapeutic medicine for anemia.

The inventive erythropoietin product can definitely be differentiated from conventional erythropoietin products in respect of several properties including the physiological activity. For example, the inventive erythropoietin product has a molecular weight of about 4,000 to about 13,000 as determined by the gel filtration method by use of a dextran gel (Sephadex) while the molecular weight of conventional erythropoietin products is in the range from 20,000 to 40,000 and the isoelectric point of the inventive erythropoietin product is from about 3.1 to about 3.6 as determined by the method of isoelectric focusing while the isoelectric point of the conventional ones is $4 \pm 0.1$.

Furthermore, the activity of the inventive product is at least 20 times stronger than the conventional products not only in the activity determination of erythropoietin by the method of bone marrow cell culture but also in the in vivo test for the increase of the red corpuscular hemoglobin when the basis of the comparison is the erythropoietin activity by the method of the polycythemic mouse assay.

The above defined novel erythropoietin product can be prepared from the crude erythropoietin obtained from the urine of healthy human, which is first adsorbed on a weakly basic anion exchanger under a neutral or weakly acidic condition in the presence of an inorganic neutral salt in a concentration of 0.1 to 0.2 mole per liter followed by the elution of the thus adsorbed effective ingredient with an aqueous solution of an inorganic neutral salt in a concentration of 0.5 to 0.7 mole per liter.

BRIEF DESCRIPTION OF THE DRAWING

The FIGURE is a graphic showing of the results of the animal test for the effectiveness of the inventive erythropoietin product taking the total dose of two times of administration as the abscissa and the concentration of hemoglobin in the blood as the ordinate.

DETAILED DESCRIPTION OF THE PREFERRED EMBODIMENTS

The starting material used in the inventive method is a crude erythropoietin product obtained from the urine of healthy human. The method for the preparation of such a crude erythropoitein product is described in detail in the above recited United States Patent. That is, the pH value of the urine of healthy human is first adjusted to 6 to 8 by adding a mineral or organic acid or an alkali such as ammonia and the erythropoietically active ingredient in the urine is then adsorbed on a specific adsorbent which is a porous polystyrene-based adsorbent resin, chitosan or diatomaceous earth followed by the elution with an organic solvent such as alcohol or an aqueous alkali solution in the case of the polystyrene adsorbent or with an aqueous alkali solution in the case of the adsorbent of chitosan or diatomaceous earth.

The thus prepared erythropoietin is a crude product and, as is mentioned before, still exhibits an inhibitory activity against erythropoiesis. No effect of purification can be obtained when this crude erythropoietin product is subjected to the procedure for purification with the condition known to be effective for the purification of the crude erythropoietin products obtained from the patient urine and the inhibitory activity against erythropoiesis cannot be reduced.

It is essential in practicing the method of the invention that the adsorption of the effective ingredient in the crude erythropoietin should be performed in the presence of an inorganic neutral salt in the adsorbate solution. Suitable inorganic neutral salts are exemplified by halides of alkali and alkaline earth metal such as sodium chloride, potassium chloride, magnesium chloride, calcium chloride, sodium bromide and the like. Sodium chloride is preferred due to the physiological safety. The concentration of these salts in the adsorbate solution is preferably in the range from about 0.1 to about 0.2 mole per liter. Lower concentration of the salt is undesirable due to the insufficient adsorption of the adsorbate. The effect of adsorption on to the anion exchanger is little affected by the kind of the inorganic neutral salts but the influencing parameter is the inoic strength of the salt in the solution.

Controlling of the pH value of the adsorbate solution in the desired range may be further facilitated by admixing a salt exhibiting a buffer action such as pyridine hydrochloride, imidazole hydrochloride and certain phosphates in order to enhance the adsorption.

The adsorbent material for the effective ingredient in the crude erythropoietin product is a weakly basic anion exchanger exemplified by diethylaminoethylated carbohydrates such as diethylaminoethylcellulose, diethylaminoethyldextran, diethylaminoethylagarose and the like. The effective ingredient in the crude erythropoietin product is most effectively adsorbed on to these anion exchangers in a neutral to weakly acidic condition. Suitable range of the pH value of the adsorbate solution is perferably from about 6.0 to about 7.5.

The effective ingredient adsorbed in the above described manner from the aqueous solution of the crude erythropoietin containing the specified inorganic neutral salt on to the weakly basic anion exchanger is, following washing with a buffer solution, then eluted out of the anion exchanger by use of an eluant solution which may be an aqueous solution of an inorganic neutral salt in a concentration of from about 0.5 to about 0.7 mole per liter. Higher concentration of the salt results in the elution of impurities. The conditions for the elution or desorption are about the same as in the adsorption excepting the concentration of the salt.

The eluate solution thus obtained can be used as such in the therapeutic purpose but, if desired, purified erythropoietin products can be separated and recovered from this solution by a conventional procedure including freeze-drying, dialysis and the like.

In accordance with the inventive method, an erythropoietin product having a high erythropoietic activity but exhibiting little inhibitive activity against erythropoiesis can be prepared in a high yield from the urine of healthy human so that a very hopeful way is opened for the therapeutical treatment of anemia patients.

Following are the examples to illustrate the inventive method for the preparation of the novel erythropoietin product as well as to illustrate the effectiveness of the inventive erythropoietin product.

In the following examples, the determination of the erythropoietin was carried out by the method of Goldwasser (see E. Goldwasser et al., Endocrinology, volume 97, 2, page 315, 1975) in which the sample under test was, after suitable dialysis or dilution, subjected to the assay of erythropoietin by the amount of the $Fe^{59}$ isotope taken into the cultured bone marrow cells of rat. The unit (U) was standardized by the calibration curve prepared by use of the working standard of erythropoietin EPWS 11 which is an erythropoietin product obtained from the urine of patients suffering from aplastic anemia followed by purification according to the method of Espada (see J. Espada, Biochem. Med., volume 3, page 475, 1970) and tested for the activity by the Cotes' method of exhypoxic polycythemic mouse assay with reference to the international reference preparation of erythropoietin (WHO Second International Reference Preparation of Erythropoietin (67/343). The determination of the protein in the erythropoietin product was undertaken by the Lowry's method (see O. B. Lowry et al., J. Biol. Chem., volume 193, page 265, 1951) with reference to a bovine serum albumin as the standard.

EXAMPLE 1

The pH value of 10 liters of the urine collected from healthy human was adjusted to 7.0 by adding a small volume of 2 N aqueous hydrochloric acid and 87 g of chitosan (FLONAC-N, a product by Kyowa Yushi Kogyo Co.) were added into the thus pH-adjusted urine followed by agitation at room temperature for 1.5 hours. The supernatant liquid portion was discarded by decantation and the chitosan was collected.

The chitosan thus having adsorbed the erythropoietin in the urine was then dispersed in 800 ml of a 0.1 M sodium carbonate buffer solution at a pH of 11 containing 0.5 mole per liter of sodium chloride and agitated for 3 hours at 7° C. followed by filtration to give an eluate solution. Salting-out of this eluate solution with ammonium sulfate gave precipitates as a crude erythropoietin product. This product having an activity of erythropoietin of 54 U/mg protein is referred to as the product A hereinafter.

Seven-weeks old female mice were each administrated with 5.3 μg of the above obtained product A over 2 days once a day each day with a half dose of the total amount as dissolved in saline, i.e. in a 0.9 w/v % sodium chloride solution, by intraperitoneal injection. The hematocrit values of the four mice thus treated as well as the other four mice administered with the same volume of the saline as the control group were determined after four days from the first administration to give the results shown in Table 1 below with statistical analysis.

TABLE 1

| Group of mice | Hematocrit value |
|---|---|
| Administrated with saline | 50.2 ± 1.9% |
| Administrated with product A | 42.5 ± 3.6% |
| | (P < 0.05) |

The above results indicate that the decrease of the hematocrit value in the mice belonging to the test group administered with the product A is significant in comparison with the control group administered with the mere physiological sodium chloride solution. The dose of the administrated activity in this case was 0.57 U per mouse or 27 U per kg of body weight since the specific activity of the product A was 54 U per mg of protein.

In the next place, 48 U of the product A were adsorbed on 2.0 ml of a diethylaminoethylcellulose (DEAE-Sephacel, a product by Pharmacia Co.) in a column from a M/80 pyridine-hydrochloric acid buffer solution at a pH of 6.5 containing 0.15 mole per liter of sodium chloride and, after washing of the adsorbent with the same buffer solution, the adsorbed ingredient was subjected to elution in two successive steps with a M/80 pyridine-hydrochloric acid buffer solution at a pH of 6.5 containing 0.3 mole per liter of sodium chloride and a M/80 pyridine-hydrochloric acid buffer solution at a pH of 6.5 containing 0.7 mole per liter of sodium chloride as the eluant solutions for the first and the second steps of the elution, respectively.

While no activity of erythropoietin was detected in the eluate solution obtained in the first step of the elution, the eluate solution from the second step exhibited the activity corresponding to 38 U of erythropoietin. This product, referred to as the product B hereinafter, had a specific activity of 372 U per mg of protein indicating a 6.9 times enrichment over the product A.

The product B above obtained was subjected to the treatment of dialysis against a 0.9 w/v % sodium chloride solution buffered at a pH of 7.4 containing 0.01 mole per liter of $Na_2HPO_4$ and $NaH_2PO_4$. The thus dialyzed erythropoietin product, which is referred to as the product B' hereinafter, was administrated to six-weeks old female mice over two days once a day each day with the same does by the intraperitoneal injection to give a total dose of 1.4 to 47 U per kg of body weight. The results of the determination of the hemoglobin concentration in the blood of each of the test animals are shown in the accompanying FIGURE by the curve B'. The FIGURE also contains the curves P and Q indicating the results obtained in the control tests undertaken by administrating the animals with the erythropoietin product prepared from the patient urine or with the mere saline, respectively.

The erythropoietin product prepared from the patient urine and used in the above control test (referred to as the product P hereinafter) was prepared by separating from the urine of patients suffering from aplastic anemia according to the method of Espada and had a specific activity of 19.4 U/mg protein. The administration of the product B' was significantly effective in increasing the hemoglobin concentration in the blood of the subject animals in comparison with the results of the control test with administration of a mere saline suggesting that the product B' had a medicinal activity with good dosage dependency of the increase in the hemoglobin concentration on the dose of administration.

On the other hand, four mice were administrated in the same manner as above each with 1 ml, corresponding to 200 ml of the raw urine, of the effluent solution obtained from the column in the adsorption of the crude erythropoietin product A on to DEAE-Sephacel as containing the unadsorbed ingredients and having been dialyzed against a physiological sodium chloride solution containing a buffer solution of M/100 $Na_2HPO_4$-$NaH_2PO_4$ at a pH of 7.4 and the concentration of hemoglobin in the blood of the animals was examined. The results are shown in Table 2 below together with the results of the control test by administrating six mice with a saline indicating that the hemoglobin concentration was significantly decreased by the administration of the unadsorbed ingredients in comparison with the saline.

TABLE 2

| Group of mice | Hemoglobin concentration in blood, g/dl |
|---|---|
| Administrated with saline | 13.8 ± 1.0 |
| Administrated with unadsorbed ingredients | 10.9 ± 1.6 (P < 0.05) |

In the above test, the solution containing the unadsorbed ingredients had no erythropoietic activity.

EXAMPLE 2

Adsorption of 97 U of the crude erythropoietin product A was carried out on to 5 ml of DEAE-Sephacel in a column from a M/100 tris-hydrochloric acid buffer solution at a pH of 6.5 containing 0.15 mole per liter of sodium chloride followed by washing with the same buffer solution and elution first with a M/100 tris-hydrochloric acid buffer solution at a pH of 6.5 containing 0.25 mole per liter of sodium chloride and then with a M/100 tris-hydrochloric acid buffer solution at a pH of 6.5 containing 0.55 mole per liter of sodium chloride.

As a result, the erythropoietin activity was recovered only in the eluate solution with the latter eluant containing 0.55 mole per liter of sodium chloride. This erythropoietin product is referred to as the product C hereinafter. The recovered erythropoietic activity of the product C was 278 U corresponding to 278% of the activity in the starting material and the specific activity was 2670 U/mg protein indicating a 49 times increase over the product A.

EXAMPLE 3

Purification of the crude erythropoietin product prepared from the urine of healthy human in the same manner as in Example 1 was undertaken with 2310 U of the crude product. Thus the crude product was adsorbed on 94 ml of a diethylaminoethyl agarose (DEAE-Sepharose CL-6B, a product by Pharmacia Co.) in a column from a M/100 imidazole-hydrochloric acid buffer solution at a pH of 6.5 containing 0.15 mole per liter of sodium chloride followed by the elution first with a M/100 imidazole-hydrochloric acid buffer solution at a pH of 6.5 containing 0.4 mole per liter of sodium chloride and then with a M/100 imidazole-hydrochloric acid buffer solution at a pH of 6.5 containing 0.6 mole per liter of sodium chloride. The erythropoietin activity was recovered in the eluate solution obtained with the latter eluant containing 0.6 mole per liter of sodium chloride. The activity of the thus recovered erythropoietin product, referred to as the product D hereinafter, was 3030 U and the specific activity thereof was 566 U/mg protein.

The activity of this product D after dialysis against a physiological sodium chloride solution at a pH of 7.4 containing M/100 $Na_2HPO_4$-$NaH_2PO_4$ was 169 I.U. as determined according to the exhypoxic polycythemic mouse assay of Cotes with reference to the calibration curve prepared with the erythropoietin working standard. The comparative results of the specific activity determination are given in Table 3 below for the products D and P as determined by the methods of the bone marrow cell culture and the exhypoxic polycythemic mouse assay.

TABLE 3

| | (U/mg protein) | | |
|---|---|---|---|
| | Activity determination by the method of | | |
| Erythropoietin | (a)* | (b)** | (a)/(b) |
| Product D | 566 | 31.5 | 18.0 |
| Product P | 19.4 | 11.3 | 1.7 |

*Bone marrow cell culture
**Exhypoxic polycythemic mouse assay

EXAMPLE 4

Four portions of each 58.0 U of the crude erythropoietin product A were each adsorbed on 2.0 ml of DEAE-Sephacel in a column under the respective different conditions as indicated in Table 4 below followed by washing first with the respective equilibrated buffer solution and then with a M/100 tris-hydrochloric acid buffer solution at pH 6.5 containing 0.15 M sodium chloride and elution with the same buffer solution but containing 0.55 M sodium chloride. The activity and the specific activity of each of the thus obtained erythropoietin products are shown in Table 4.

TABLE 4

| No. | Conditions of adsorption | Activity, U | Specific activity, U/mg protein |
|-----|--------------------------|-------------|--------------------------------|
| 1 | M/100 $Na_2HPO_4$—$NaH_2PO_4$, 0.1 M NaCl, pH 6.5 | 47.7 | 832 |
| 2 | M/100 $Na_2HPO_4$—$NaH_2PO_4$, 0.15 M NaCl, pH 6.0 | 29.9 | 1263 |
| 3 | M/100 $Na_2HPO_4$—$NaH_2PO_4$, 0.15 M NaCl, pH 7.0 | 62.6 | 501 |
| 4 | M/100 $Na_2HPO_4$—$NaH_2PO_4$, 0.15 M NaCl, pH 7.5 | 20.9 | 759 |

As is clear from Table 4, the specific activity of the thus recovered erythropoietin products was remarkably increased by 9.3 to 23 times over the value of 54 U/mg protein of the product A although the recovery of the activity was somewhat decreased depending on the conditions of adsorption.

Comparative Example 1

Adsorption of a crude erythropoietin product having an activity of 113 U obtained from the urine of healthy human by the method of Espada was carried out on to 14.3 ml of DEAE-Sephacel from a M/100 tris-hydrochloric acid buffer solution at a pH of 7.0 followed by the elution successively with aqueous solutions of calcium chloride in concentrations of 5, 30 and 100 m moles per liter.

The effluent solution obtained in the step of adsorption containing the unadsorbed ingredients and the eluate solution with the calcium chloride eluant of 100 m moles per liter concentration both exhibited the erythropoietic activity. The activities of the solutions were 48 U in the former and 52 U in the latter with specific activities of 4.5 and 1.8 U/mg protein, respectively.

Comparative Example 2

Adsorption of 5.5 U of the crude erythropoietin product A was carried out on to 1.5 ml of a diethylaminoethyl dextran (Diethylaminoethyl Sephadex A-50, a product by Pharmacia Co.) from a M/100 tris-hydrochloric acid buffer solution at a pH of 7.0 followed by elution first with an aqueous solution of calcium chloride in a concentration of 15 m moles per liter and then with a 4% ammonia water.

The effluent solution obtained in the step of adsorption containing the unadsorbed ingredients and the eluate solution with the 4% ammonia water both exhibited the erythropoietic activity. The activities of these solutions were 3.3 U in the former and 3.0 U in the latter with the specific activities of 49.7 and 50.6 U/mg protein, respectively.

Comparative Example 3

Adsorption of 185 U of the crude erythropoietin product A was carried out on to 11 ml of DEAE-Sephacel from a M/100 $Na_2HPO_4$-$NaH_2PO_4$ buffer solution at a pH of 6.0 followed by the elution with an aqueous solution of sodium chloride in a concentration of 0.25 mole per liter.

The effluent solution obtained in the step of adsorption containing the unadsorbed ingredients and the eluate solution with the sodium chloride eluant both exhibited the erythropoietic activity. The activities in these solutions were 30 U in the former and 69 U in the latter while the specific activity in the latter solution was 48.5 U/mg protein indicating that almost no effect of purification had been obtained.

What is claimed is:

1. A method for the preparation of an erythropoietin product having no inhibitory effect against erythropoiesis which comprises the steps of
   (a) adsorbing a crude erythropoietin product obtained from the urine of healthy human on to a weakly basic anion exchanger from a neutral or weakly acidic aqueous solution in the presence of an inorganic neutral salt in a concentration in the range from 0.1 to 0.2 mole per liter, and
   (b) eluting the thus adsorbed erythropoietin product with an aqueous eluant solution containing an inorganic neutral salt in a concentration in the range from 0.5 to 0.7 mole per liter.

2. The method as claimed in claim 1 wherein the inorganic neutral salt used in step (a) is selected from the group consisting of sodium chloride, potassium chloride, magnesium chloride, calcium chloride and sodium bromide.

3. The method as claimed in claim 1 wherein the weakly basic anion exchanger is a diethylaminoethylated carbohydrate.

4. The method as claimed in claim 3 wherein the diethylaminoethylated carbohydrate is selected from the group consisting of diethylaminoethyl cellulose, diethylaminoethyl dextran and diethylaminoethyl agarose.

5. The method as claimed in claim 1 wherein the neutral or weakly acidic aqueous solution has a pH in the range from 6.0 to 7.5.

6. The method as claimed in claim 1 wherein the aqueous eluant solution had a pH in the range from 6.0 to 7.5.

7. An erythropoietin product having no inhibitory effect against erythropoiesis with a molecular weight in the range from 4,000 to about 13,000 and an isoelectric point in the range from 3.1 to 3.6.

* * * * *